United States Patent
Zhou et al.

(10) Patent No.: US 11,287,410 B2
(45) Date of Patent: *Mar. 29, 2022

(54) SAMPLING PUMPS AND GAS ANALYZERS

(71) Applicant: Shenzhen Mindray Bio-Medical Electronics Co., Ltd., Shenzhen (CN)

(72) Inventors: Weidong Zhou, Shenzhen (CN); Zhonghua Liu, Shenzhen (CN); Yunfeng Liu, Shenzhen (CN); Jian Cen, Shenzhen (CN); Heng Chen, Shenzhen (CN); Guangqi Huang, Shenzhen (CN); Joakim Carl Gabrielsson, Shenzhen (CN); Johan Nils Ernst Werner, Shenzhen (CN); Peter Erik Axel Svedmyr, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 86 days.

This patent is subject to a terminal disclaimer.

(21) Appl. No.: 16/878,243

(22) Filed: May 19, 2020

(65) Prior Publication Data

US 2020/0278334 A1 Sep. 3, 2020

Related U.S. Application Data

(63) Continuation of application No. 14/334,429, filed on Jul. 17, 2014, now Pat. No. 10,656,132, which is a
(Continued)

(30) Foreign Application Priority Data

Jan. 19, 2012 (CN) .................. 201210018139.X

(51) Int. Cl.
*F04B 41/06* (2006.01)
*F04B 27/12* (2006.01)
(Continued)

(52) U.S. Cl.
CPC ......... *G01N 33/0073* (2013.01); *F04B 13/00* (2013.01); *F04B 23/06* (2013.01);
(Continued)

(58) Field of Classification Search
CPC .................................................. F04B 43/0736
See application file for complete search history.

(56) References Cited

U.S. PATENT DOCUMENTS 3,816,029 A * 6/1974 Bowen .................. F03C 1/08
417/223
4,359,312 A 11/1982 Funke
(Continued)

FOREIGN PATENT DOCUMENTS

| CN | 1281527 A | 11/2001 |
| CN | 201843759 U | 5/2011 |
| CN | 102305203 A | 1/2012 |

*Primary Examiner* — Herbert K Roberts
(74) *Attorney, Agent, or Firm* — Kory D. Christensen

(57) ABSTRACT

Provided are sampling pumps and gas analyzers using the sampling pumps. The sampling pump may include at least one reciprocating pump set and a control system. Each reciprocating pump set can include two reciprocating pumps. The control system can output drive signals for controlling reciprocating drawing and compressing operations of the reciprocating pumps, where the control system
(Continued)

may be designed to output the drive signals that cause the two reciprocating pumps within the same set to provide opposing impact directions at the same time.

20 Claims, 3 Drawing Sheets

Related U.S. Application Data continuation of application No. PCT/CN2012/087485, filed on Dec. 26, 2012.

(51) Int. Cl.
| | | |
|---|---|---|
| *G01N 33/00* | (2006.01) | |
| *G01N 1/24* | (2006.01) | |
| *F04B 53/00* | (2006.01) | |
| *F04B 23/06* | (2006.01) | |
| *F04B 13/00* | (2006.01) | |
| *G01N 33/497* | (2006.01) | |
| *F04B 43/073* | (2006.01) | |

(52) U.S. Cl.
CPC ............. *F04B 27/12* (2013.01); *F04B 41/06* (2013.01); *F04B 53/001* (2013.01); *G01N 1/24* (2013.01); *G01N 33/497* (2013.01); *F04B 43/0736* (2013.01)

(56) References Cited

U.S. PATENT DOCUMENTS

| | | | | |
|---|---|---|---|---|
| 4,386,888 A * | 6/1983 | Verley | ............... | F04B 43/06 417/393 |
| 4,488,853 A * | 12/1984 | Benson | ............... | F01B 11/00 417/240 |
| 4,681,513 A * | 7/1987 | Saito | ............... | F04B 1/02 417/18 |
| 5,354,180 A * | 10/1994 | Forster | ............... | F04B 1/22 417/199.1 |
| 5,818,131 A * | 10/1998 | Zhang | ............... | F04D 29/048 310/15 |
| 5,944,302 A * | 8/1999 | Loc | ............... | F16F 1/02 267/180 |
| 6,293,756 B1 * | 9/2001 | Andersson | ............... | F04B 11/0058 417/3 |
| 2005/0061722 A1 | 3/2005 | Takao | | |
| 2007/0034792 A1* | 2/2007 | Zhang | ............... | G01N 21/3504 250/252.1 |
| 2011/0020156 A1* | 1/2011 | Van Brunt | ............... | F04B 17/04 417/416 |
| 2011/0223581 A1* | 9/2011 | Stobbe | ............... | F04B 45/0536 435/3 |
| 2014/0326042 A1* | 11/2014 | Zhou | ............... | G01N 1/24 73/23.3 |

* cited by examiner

SAMPLING PUMPS AND GAS ANALYZERS

CROSS-REFERENCE TO RELATED APPLICATIONS

This application is a continuation of U.S. patent application Ser. No. 14/334,429, filed Jul. 17, 2014, for SAMPLING PUMPS AND GAS ANALYZERS, which is a continuation of Patent Cooperation Treaty Application No. PCT/CN2012/087485, filed Dec. 26, 2012, which claims the benefit of priority to Chinese Patent Application 201210018139.X, filed Jan. 19, 2012, each of which are hereby incorporated by reference.

TECHNICAL FIELD

This disclosure generally relates to respiration monitoring in the medical field and particularly to sampling pumps and gas analyzers using the sampling pumps.

BACKGROUND

Sampling pumps that are widely used for respiration monitoring in medical equipment or modules, such as gas measurement modules, can extract a gas sample from a patient's breathing circuit and convey the extracted gas to respiration monitoring equipment, so that the respiration monitoring equipment can monitor the composition of the gas exhaled by the patient in real time, thereby allowing medical staff to evaluate the patient's vital signs. The gas sensor probe for gas measurement used in respiration monitoring equipment is a precision instrument, and its measurement accuracy can be affected by vibrational interference that may be present during operation. The sampling pump is often a main vibration source in the respiratory monitoring module. The gas sensor can also be sensitive to flow fluctuations of the monitored gas. If the gas sensor experiences large flow fluctuations, some measurement noise may occur, which can also affect measurement accuracy. Therefore, the sampling pump should provide stable sampling flow.

A diaphragm sampling pump using a single rotary motor is often used for gas sampling in existing respiration monitoring equipment. Due to its working principle, the diaphragm pump usually has both relatively large flow fluctuations and some vibrations during sampling. A single linear reciprocating pump may produce larger vibrations, and thus it is not typically used in respiration monitoring equipment.

SUMMARY OF THIS DISCLOSURE

This disclosure provides sampling pumps for delivering fluid and reducing vibration and provides gas analyzers for gas detection and analysis that use such sampling pumps.

In one aspect, a sampling pump may include at least one reciprocating pump set and a control system. Each reciprocating pump set can include two reciprocating pumps. The control system can output drive signals for controlling reciprocating drawing and compressing operations of the reciprocating pumps, where the control system may be designed to output the drive signals that can cause the two reciprocating pumps within the same set to provide opposing impact directions at the same time.

In some embodiments, the two reciprocating pumps can be fixedly mounted in such a way that the impact directions generated by the two reciprocating pumps may be along the same line (i.e., a common line).

In some embodiments, the two reciprocating pumps within the same set can be linear reciprocating pumps with the same or substantially the same impact force.

In some embodiments, the two reciprocating pumps within the same set can be rigidly fixed along the same line and in the same orientations. The drive signals provided to the two reciprocating pumps can have the same amplitude and a phase deviation of about 180°.

In some embodiments, the two reciprocating pumps within the same set can be rigidly fixed along the same line and in opposing orientations. The drive signals provided to the two reciprocating pumps can have the same amplitude and phase.

In some embodiments, the two reciprocating pumps within the same set can be directly, rigidly and fixedly connected to each other to form an integral structure.

In some embodiments, the sampling pump may also include at least one connection carrier, where the two reciprocating pumps within the same set can be rigidly and fixedly mounted on the same connection carrier.

In some embodiments, the connection carrier may be a connection plate that is affixed to side surfaces of the reciprocating pumps.

In some embodiments, the sampling pump may also include at least one integrated output channel. The integrated output channel can communicate with output channels of the two reciprocating pumps within the same set so as to gather fluid outputted from the two reciprocating pumps within the same set.

In another aspect, a gas analyzer may include a gas measurement module for detecting and analyzing some extracted gas, and a sampling pump described above for providing the gas measurement module with the gas to be measured.

In some embodiments, the gas analyzer may also include a gas circuit, where the gas circuit can include at least two gas outlets and at least one integrated output channel. The two gas outlets can communicate with the integrated output channel, and output channels of the two reciprocating pumps within the same set can communicate with corresponding gas outlets.

BRIEF DESCRIPTION OF THE DRAWINGS

The following detailed descriptions of respective embodiments in this disclosure can be understood better when combining with these figures, in which the same structure is represented by the same reference sign. In the figures.

DETAILED DESCRIPTION

This disclosure is further described below in detail with reference to the figures and specific implementations.

In various embodiments of this disclosure, a sampling pump may include at least one reciprocating pump set, where each reciprocating pump set may include two reciprocating pumps that are fixedly mounted along the same or common line. Herein, the two reciprocating pumps within the same set can provide impact forces in opposing directions at the same time by configuring drive signals used to control reciprocating drawing and compressing operations of the reciprocating pumps, so that the impact forces caused by the movements of the reciprocating pumps can be counter-balanced and some vibrations correspondingly generated can be reduced.

The reciprocating pump in this disclosure can be a rotary motor reciprocating pump driven by a rotary motor, and it can also be a linear reciprocating pump driven by a driving device capable of outputting linear reciprocating movement directly. For example, a diaphragm pump using a voice coil linear motor or any other driving device capable of outputting linear reciprocating movement can be used as the linear reciprocating pump. Two reciprocating pumps within the same set can be fixedly mounted along the same line, as a result of which the impact force that is generated by one reciprocating pump when acting on fluid(s) can be transferred and applied to the other reciprocating pump. Through further regulation and/or control, the two reciprocating pumps within the same set can provide opposing impact directions at the same time, so that their respective impact forces may be completely or mostly counter-balanced, and thus some vibrations caused by the impact forces of the reciprocating pumps during their operation can also be counter-balanced, thereby ensuring stable operations of the reciprocating pump set and the sampling pump using the same. Herein, the fluid(s) can be a gas, liquid or mixture thereof.

In an embodiment, the two reciprocating pumps within the same set can be rigidly and fixedly connected with each other so as to transfer their impact forces and vibrations. In some cases, the two reciprocating pumps can be directly and rigidly fixed together to form an integral structure. In some cases, the sampling pump can also include a third connection carrier such as a connection plate, a base or the like, where the two reciprocating pumps can both be rigidly and fixedly mounted onto the third connection carrier.

Figure 1:
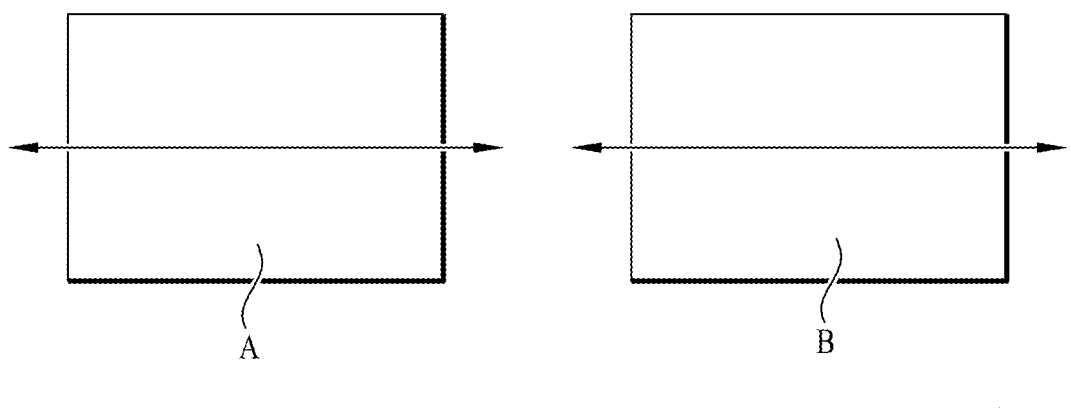
FIG. 1 is a schematic diagram showing the locations of two linear reciprocating pumps in accordance with an embodiment of this disclosure.

The two reciprocating pumps within the same set can be arranged next to each other, so that their respective impact forces can be at least partially counter-balanced. In an embodiment, the two reciprocating pumps within the same set are arranged next to each other and along the same line. In this case, the impact forces and the vibrations generated by the two reciprocating pumps can be maintained along the same line to counteract with each other. Referring to FIG. 1, A represents a front linear reciprocating pump, and B represents a rear reciprocating pump, while the pumps A and B are arranged on the same straight line. The arrows in FIG. 1 refer to impact and vibration directions generated by the linear reciprocating pumps. When a control system controls the pump A to generate leftward or rightward impact force, the control system may correspondingly control the pump B to generate impact force in an opposing direction (i.e., rightward or leftward respectively), in which case their respective impact forces can completely, substantially or partially counter-balance with each other.

The two reciprocating pumps within the same set are required to provide opposing impact directions at the same time. For this purpose, the control system can send drive signals having coordinated driving commands to the two reciprocating pumps so as to control their respective drawing and compressing timings. The drive signals can be current signals, voltage signals or any other suitable signals.

Using the case where the two reciprocating pumps are both linear reciprocating pumps as an example, since linear reciprocating pumps may be directly driven by a driving device capable of outputting linear reciprocating movements, the control system can send drive signals that have the same amplitude(s) as well as the same or opposing phase(s) to the two linear reciprocating pumps, so that the driving devices inside the two linear reciprocating pumps can achieve coordinated operations.

Figure 2:
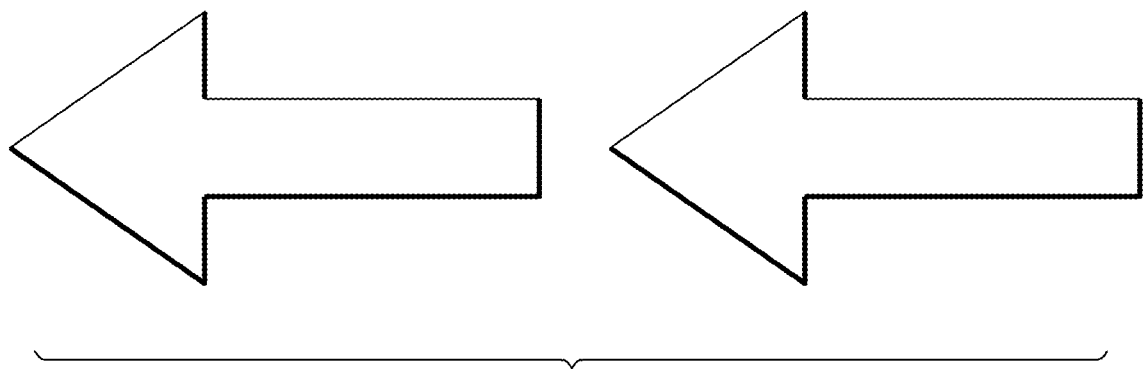
FIG. 2 is a schematic diagram showing the orientations of two linear reciprocating pumps in accordance with an embodiment of this disclosure.

In an embodiment, the two linear reciprocating pumps within the same set are both rigidly fixed along the same line and mounted to have the same orientations. The impact forces respectively generated by the two linear reciprocating pumps during their drawing and/or compressing operations can be the same (or substantially the same), or can have an allowable difference within a specified range (the specified range can be manually set according to actual needs). Here, the orientation of the reciprocating pump refers to a movement direction outputted by the driving device inside the reciprocating pump when fluid is compressed out of the reciprocating pump. For example, the arrows in FIG. 2 respectively represent the movement directions outputted by the driving devices inside the two linear reciprocating pumps when fluid is respectively compressed out of both linear reciprocating pumps. In this embodiment, the directions shown by the arrows can be defined as the orientations of the linear reciprocating pumps, where the two linear reciprocating pumps have the same orientations as shown in FIG. 2. It is noted that when the fluid is drawn into the linear reciprocating pump, the movement direction outputted by the driving device inside the linear reciprocating pump is opposite to the orientation of the linear reciprocating pump. In this embodiment, the two linear reciprocating pumps within the same set may often be equally designed in their impact responses, and their drive signals may also be the same in amplitude. Therefore, when the fluid is drawn into or compressed out of the two linear reciprocating pumps under the control of the drive signals, the impact forces generated from the movements of the two linear reciprocating pumps can also be the same (or substantially the same). Here, the drive signals with alternative directions can be transmitted from the control system to the two linear reciprocating pumps; that is, those drive signals that have the same amplitudes and the opposing phases (i.e., with a phase deviation of about) 180° can be respectively provided to the two linear reciprocating pumps. Under the control of the drive signals, the driving device inside one of the two linear reciprocating pumps may move to the left while the driving device inside the other linear reciprocating pump may move to the right, and vice versa; that is, one of the two linear reciprocating pumps is drawing the fluid while the other one is compressing the fluid out, and vice versa. The movement directions of the driving devices inside the two linear reciprocating pumps are maintained to be opposite to each other at any time. In this way, the impact vibrations generated by the two linear reciprocating pumps along opposing directions can counter-balance with each other, and thus stable operation can be achieved for the sampling pump.

Figure 3:
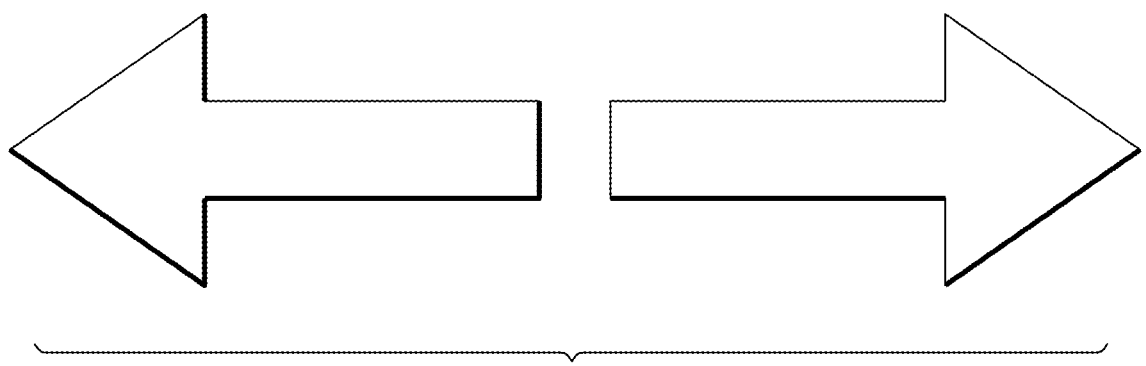
FIG. 3 is a schematic diagram showing the orientations of two linear reciprocating pumps in accordance with another embodiment of this disclosure.

In another embodiment shown in FIG. 3, the arrows respectively represent the movement directions outputted by the driving devices inside the two linear reciprocating pumps when fluid is respectively compressed out of both linear reciprocating pumps. Here, an arrow also indicates the orientation of a linear reciprocating pump, and thus the two linear reciprocating pumps in this embodiment may have opposing orientations represented by the opposing arrows. Also as discussed above, when some fluid is drawn into the linear reciprocating pump, the movement direction outputted by the driving device inside the linear reciprocating pump is opposite to the orientation of the linear reciprocating pump. In this case, the control system may send the same drive signals (i.e., with the same amplitude and phase) to the two linear reciprocating pumps, so that the two linear reciprocating pumps can have the same drawing and compressing timings. That is, when one of the linear reciprocating pumps is drawing the fluid, the other linear reciprocating pump is also drawing the fluid. In this situation, since the two linear reciprocating pumps have opposing orientations, the movement directions outputted by their internal driving devices can be opposite to each other, and thus the impact vibrations may also be generated in opposing directions. Therefore, such impact vibrations can counter-balance with each other, thereby achieving stable operation for the sampling pump.

When a rotary motor reciprocating pump is in operation, its output component (such as plunger or piston) may also generate some reciprocating impact when acting upon fluid. In an embodiment, the control system can be used to output the drive signals to two rotary motor reciprocating pumps to control the rotation timings of the rotary motors inside. In this way, the timings for linear reciprocating movements can be adjusted for the output components inside the reciprocating pumps.

In some embodiments, the reciprocating pump set can include one linear reciprocating pump and one rotary motor reciprocating pump.

In an embodiment, output channels (i.e., fluid outlets) of the two reciprocating pumps within the same set can be assembled together to form an integrated output channel. The integrated output channel can communicate with the output channels of both reciprocating pumps within the same set, and thus the fluid may be outputted through the integrated output channel uniformly. When the two linear reciprocating pumps have the same orientations and their output channels are assembled into the integrated output channel, the fluid flow resulting from the two linear reciprocating pumps may be stable with substantially no fluctuations by forming peak-to-valley compensation in the case where one linear reciprocating pump is drawing the fluid while the other linear reciprocating pump is compressing the fluid out.

The sampling pumps described in various embodiments of this disclosure may also include multiple reciprocating pump sets. The multiple reciprocating pump sets may be separately arranged, or may also be rigidly and fixedly connected to one another. In some embodiments, a part of the multiple reciprocating pump sets may be separately arranged, while the remaining reciprocating pump sets may be in rigid and fixed connection to one another.

The sampling pump will be further illustrated from the following descriptions, where gas is used as the fluid and a linear reciprocating pump is used as the reciprocating pump by way of example.

Figure 4:
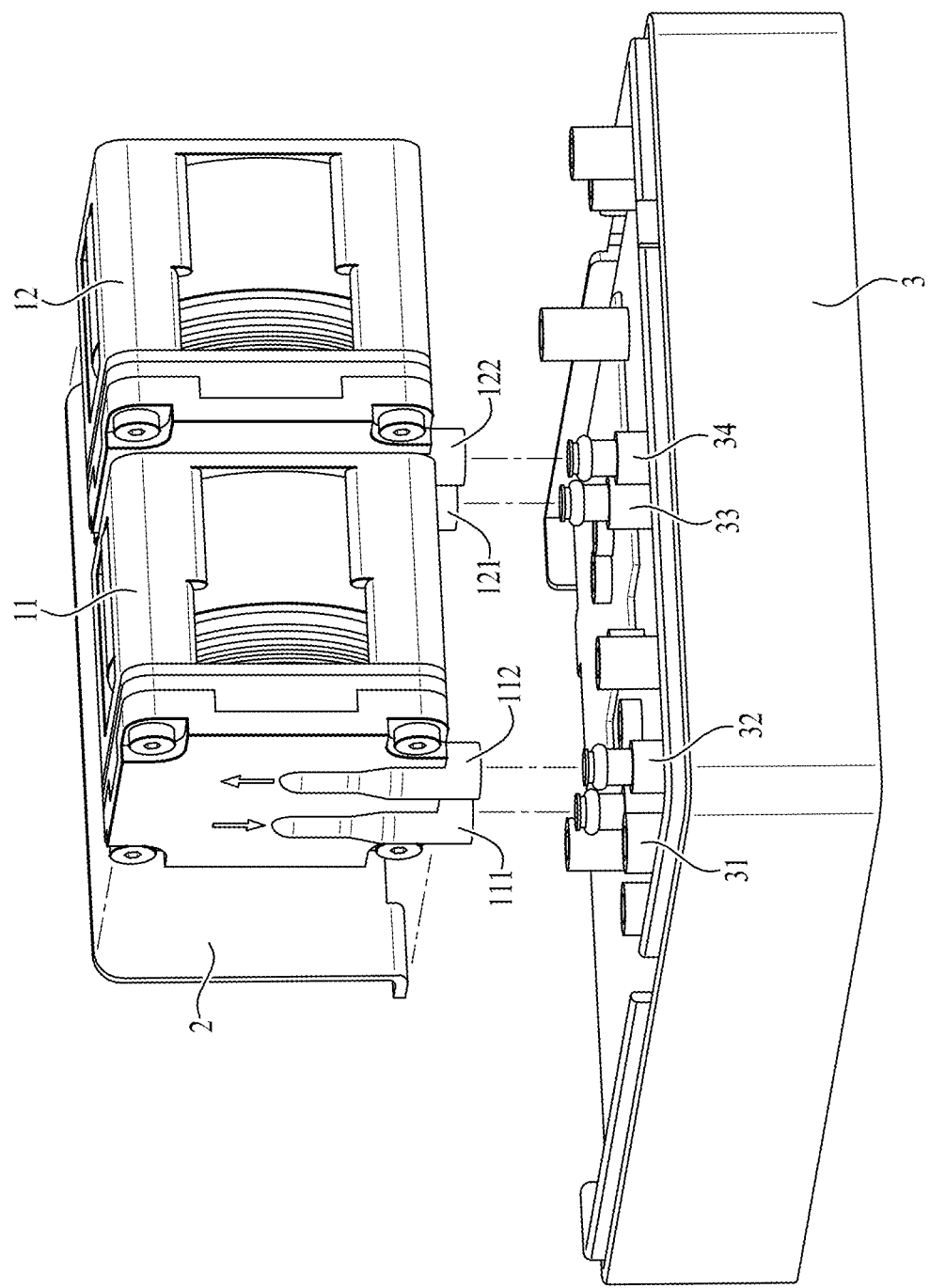
FIG. 4 shows a structure in accordance with an embodiment of this disclosure.

Referring to FIG. 4, a sampling pump may include a control system (not shown here), two linear reciprocating pumps 11, 12 and a connection plate 2. Each of the linear reciprocating pumps 11, 12 can be respectively provided with an inlet nozzle 112, 122 as a fluid input channel and an outlet nozzle 111, 121 as a fluid output channel. The two linear reciprocating pumps 11, 12 can be rigidly affixed onto the connection plate 2, and thus the two linear reciprocating pumps 11, 12 and the connection plate 2 may form an integral structure.

In this embodiment, the two linear reciprocating pumps 11, 12 may have the same orientations. Based on this arrangement, the control system can coordinate operation timings of the two reciprocating pumps 11, 12 via the drive signals that have the same amplitude but opposing phase (i.e., with a phase deviation of about 180°). In this way, movement directions outputted by the motors of the two linear reciprocating pumps 11, 12 can be opposite to each other at any time. As a result, impact vibrations generated along opposing directions by the two linear reciprocating pumps 11, 12 can be counter-balanced (or mostly counter-balanced).

The outlet nozzles 111, 121 of the two linear reciprocating pumps 11, 12 can further be assembled together to form an integrated output channel. Since the two linear reciprocating pumps 11, 12 may compress the gas out in alternate fashion, their alternating gas flows may combine to correspond to overlapping peaks and valleys. As a result, stable flow can be achieved and fluid fluctuations can be greatly reduced during fluid delivery.

Figure 5:
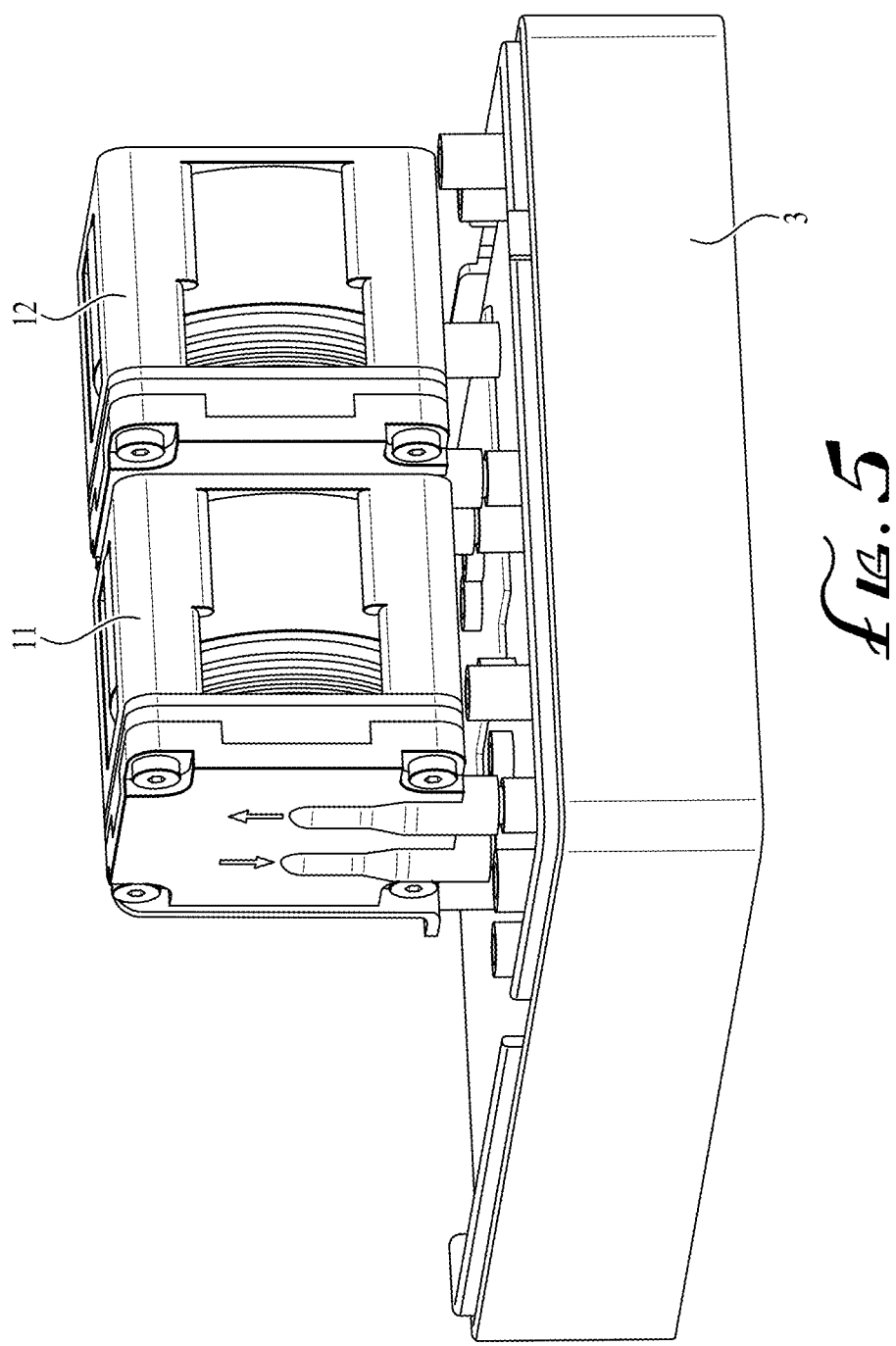
FIG. 5 shows a structure in accordance with another embodiment of this disclosure.

FIG. 5 also shows an embodiment of this disclosure. Unlike the embodiment shown in FIG. 4, there is no connection plate in this embodiment; instead, the two linear reciprocating pumps 11, 12 are directly, rigidly and fixedly connected along an axial direction to form an integral structure.

The sampling pumps described in various embodiments above can be applied to any fluid analyzers or any fluid measurement equipment. For example, a gas analyzer with such sampling pumps can be provided.

In an example embodiment (such as FIG. 4), a gas analyzer can include a gas measurement module and any one of the above-described sampling pumps. The gas measurement module can be used for gas detection and analysis. Any existing or future techniques that can achieve gas detection and analysis can be employed for the gas measurement module. The sampling pump can deliver the gas to be detected and analyzed from a gas source to the gas measurement module.

The gas analyzer in this embodiment may also include a base 3 and one or more gas circuits (not shown here). The reciprocating pump set can be fixedly mounted on the base 3, and the gas circuit(s) can be fixedly mounted on or inside the base 3. The gas circuit(s) can include two sets of gas inlets 32, 34 and gas outlets 31, 33, where the two gas outlets 31, 33 may communicate to form a larger gas outlet for gathering the gas outputted from the two linear reciprocating pumps 11, 12. In this regard, the two gas inlets 32, 34 may also communicate with each other. The gas sensor(s) within the gas analyzer is a precision instrument that is not only sensitive to external vibrations but also to fluctuations of gas flow. If the fluid has large fluctuations when passing through the gas sensor(s), measurement noise that affects measurement accuracy may occur. For these reasons, two reciprocating pumps having symmetrical (i.e., opposing) impact effects can be employed in this embodiment. On one hand, impact vibrations can be reduced during operation so as to realize stable gas delivery and improve the measurement accuracy of the gas sensor(s). On the other hand, the sampling pump in this embodiment may use alternative drive timings for gas sampling, in which case the gas can be outputted stably and flow fluctuations can be significantly reduced from the gas circuit(s), thereby further improving the measurement accuracy of the gas sensor(s).

In some alternative embodiments of this disclosure, two reciprocating pumps within the same set may not be arranged along the same line. Instead, based on the technical solutions herein to solve the involved vibration problem, any suitable arrangement can be used for the two reciprocating pumps as long as their impact forces have opposing directions so as to achieve absorption of vibration to a certain extent.

This disclosure is described above as detailed illustrations with reference to specific implementations, while this disclosure should not be limited to these illustrations. For those of ordinary skill in the art, various conclusions or equivalents may be made without departing from the concept of this disclosure, while such conclusions or equivalents should be deemed to be included within the scope of this disclosure.

The invention claimed is:

1. A sampling pump, comprising:
   at least one connection carrier;
   at least one reciprocating pump set comprising two reciprocating pumps,
      wherein each of the two reciprocating pumps comprises a rotary motor and an outlet nozzle,
      wherein the two reciprocating pumps are separated and mounted on the at least one connection carrier;
   a base separated from the at least one connection carrier, wherein the at least one connection carrier and the two reciprocating pumps are mounted on the base;
   a control system in operable communication with each of the two reciprocating pumps and operable for outputting drive signals to the rotary motor of each of the two reciprocating pumps, wherein the drive signals cause the two reciprocating pumps within a same reciprocating pump set to simultaneously provide opposing impact force directions; and
   at least one integrated output channel comprising each outlet nozzle of the two reciprocating pumps.

2. The sampling pump of claim 1, wherein the drive signals have identical amplitudes and different or identical phases depending on whether the two reciprocating pumps are in a same or opposing orientation, respectively, along a common line to cause the two reciprocating pumps within the same reciprocating pump set to simultaneously provide opposing impact force directions.

3. The sampling pump of claim 2, wherein the two reciprocating pumps within the same set are in a same orientation, wherein the drive signals provided to each of the two reciprocating pumps have identical amplitudes and a phase deviation of about 180°.

4. The sampling pump of claim 2, wherein the two reciprocating pumps within the same set are in an opposing orientation, and wherein the drive signals provided to each of the two reciprocating pumps have identical phases.

5. The sampling pump of claim 1, wherein the two reciprocating pumps within the same set are linear reciprocating pumps with an identical impact force.

6. The sampling pump of claim 1, wherein the at least one connection carrier is a connection plate that is affixed to side surfaces of the two reciprocating pumps in the same set.

7. The sampling pump of claim 1, wherein the at least one connection carrier and the two reciprocating pumps forms an integral structure.

8. The sampling pump of claim 1, wherein the at least one integrated output channel communicates to each outlet nozzle of the two reciprocating pumps within the same set.

9. The sampling pump of claim 1, further comprising at least two gas outlets mounted on the base.

10. The sampling pump of claim 9, wherein the at least two gas outlets are coupled to the at least one integrated output channel to gather a gas outputted from the two reciprocating pumps.

11. A gas analyzer, comprising:
    a gas measurement module for gas detection and analysis; and
    a sampling pump for providing the gas measurement module with gas to be measured, wherein the sampling pump comprises:
       at least one connection carrier;
       at least one reciprocating pump set comprising two reciprocating pumps,
          wherein each of the two reciprocating pumps comprises a rotary motor and an outlet nozzle,
          wherein the two reciprocating pumps are separated and mounted on the at least one connection carrier;
       a base separated from the at least one connection carrier, wherein the at least one connection carrier and the two reciprocating pumps are mounted on the base;
       a control system in operable communication with each of the two reciprocating pumps and operable for outputting drive signals to each rotary motor of the two reciprocating pumps, wherein the drive signals cause the two reciprocating pumps within a same reciprocating pump set to simultaneously provide opposing impact force directions; and
       at least one integrated output channel comprising each outlet nozzle of the two reciprocating pumps.

12. The gas analyzer of claim 11, wherein the two reciprocating pumps within the same set are linear reciprocating pumps with an identical impact force.

13. The gas analyzer of claim 11, wherein the drive signals have identical amplitudes and different or identical phases depending on whether the two reciprocating pumps are in a same or opposing orientation, respectively, along a common line to cause the two reciprocating pumps within the same reciprocating pump set to simultaneously provide opposing impact force directions.

14. The gas analyzer of claim 13, wherein the two reciprocating pumps within the same set are in a same orientation, wherein the drive signals provided to each of the two reciprocating pumps have identical amplitudes and a phase deviation of about 180°.

15. The gas analyzer of claim 13, wherein the two reciprocating pumps within the same set are in an opposing orientation, and wherein the drive signals provided to each of the two reciprocating pumps have identical phases.

16. The gas analyzer of claim 11, wherein the at least one connection carrier is a connection plate that is affixed to side surfaces of the two reciprocating pumps in the same set.

17. The gas analyzer of claim 11, wherein the at least one connection carrier and the two reciprocating pumps forms an integral structure.

18. The gas analyzer of claim 11, wherein the at least one integrated output channel communicates to each outlet nozzle of the two reciprocating pumps within the same set.

19. The gas analyzer of claim 11, further comprising at least two gas outlets mounted on the base.

20. The gas analyzer of claim 19, wherein the at least two gas outlets are coupled to the at least one integrated output channel to gather the gas outputted from the two reciprocating pumps.

* * * * *